(12) United States Patent
Plannerer

(10) Patent No.: US 7,043,784 B2
(45) Date of Patent: May 16, 2006

(54) PATIENT EXAMINATION SUPPORT SYSTEM

(75) Inventor: Jürgen Plannerer, Kemnath (DE)

(73) Assignee: Siemens Aktiengesellschaft, Munich (DE)

( * ) Notice: Subject to any disclaimer, the term of this patent is extended or adjusted under 35 U.S.C. 154(b) by 2 days.

(21) Appl. No.: 10/858,784

(22) Filed: Jun. 2, 2004

(65) Prior Publication Data

US 2004/0261176 A1 Dec. 30, 2004

(30) Foreign Application Priority Data

Jun. 4, 2003 (DE) ................................ 103 25 301

(51) Int. Cl.
*H05G 1/02* (2006.01)
*A61B 6/04* (2006.01)

(52) U.S. Cl. .......................................... 5/601; 378/209

(58) Field of Classification Search .................... 5/601; 378/209, 206, 195, 196, 208
See application file for complete search history.

(56) References Cited

U.S. PATENT DOCUMENTS

| | | | |
|---|---|---|---|
| 5,490,296 A | | 2/1996 | Fleury et al. |
| 5,825,843 A | * | 10/1998 | Kobayashi .................... 378/20 |
| 6,416,219 B1 | * | 7/2002 | Pflaum et al. ............... 378/209 |
| 6,574,808 B1 | * | 6/2003 | Brown et al. .................... 5/601 |
| 6,865,411 B1 | * | 3/2005 | Erbel et al. ................. 600/407 |
| 2002/0104163 A1 | * | 8/2002 | Reimann ........................ 5/601 |
| 2004/0261177 A1 | * | 12/2004 | Hoth et al. ..................... 5/601 |

FOREIGN PATENT DOCUMENTS

| | | |
|---|---|---|
| DE | 199 20 008 A1 | 12/2000 |
| EP | 0 151 910 B1 | 12/1984 |

\* cited by examiner

*Primary Examiner*—Michael Trettel
(74) *Attorney, Agent, or Firm*—Brinks Hofer Gilson & Lione

(57) ABSTRACT

A patient examination support system comprising an examination tabletop adjustable in vertical and in longitudinal directions, and a lifting structure which supports the examination tabletop. A treatment or diagnosis area is spaced apart in the longitudinal direction of the examination tabletop from a lifting structure, and the lifting structure has a height compensation device for compensating for a sagging of the examination tabletop when loaded by a patient of predetermined stature in a predetermined way, in the treatment or diagnosis area.

14 Claims, 2 Drawing Sheets

PATIENT EXAMINATION SUPPORT SYSTEM

BACKGROUND

The invention relates, in general, to clinical patient tables or support systems, and more particularly to a patient examination support system, which has an examination table or tabletop that is adjustable in vertical and in longitudinal directions, and in which a treatment or diagnosis area is spaced apart in the longitudinal direction of the examination table from a lifting device that supports the examination tabletop.

Such patient examination support systems are known, for instance, from German Patent Disclosure DE 199 20 008 A1, as a part of a surgical diagnosis system, from U.S. Pat. No. 5,490,296, or from European Patent Disclosure EP 0 151 910.

In a computed tomography or angiography examination, the patient is typically on an examination tabletop which protrudes past a supporting load-bearing structure, in particular a lifting structure, and is adjustable in the longitudinal direction. A weight of the patient may cause a slight sagging of the examination tabletop, which may hinder or reduce the accuracy of an imaging process that may be specifically required in conjunction with radiation therapy procedures.

Reinforcing the examination tabletop, particularly in an X-ray system, may additionally affect a beam path in the examination area and thus once again impair a quality of the imaging process. Another possible way of increasing stability of the examination tabletop could be an altered distribution of mass, for instance in the form of a profile section or hollow struts of the examination tabletop. Such altered and uneven mass distribution within the examination table, however, would increase a risk of artifacts in the imaging process, particularly in computed tomography (CT).

OBJECT AND SUMMARY

The present invention is defined by the following claims. This description summarizes some aspects of the present embodiments and should not be used to limit the claims.

An object is to disclose a patient examination support system that is especially well suited for x-ray diagnosis processes and that is distinguished by a substantially attainable precision.

This object is attained by a patient examination support system which has an examination tabletop that is adjustable in vertical and longitudinal directions and in which a treatment or diagnosis area is spaced apart in the longitudinal direction of the examination tabletop. A lifting structure supports the examination table, wherein the lifting structure may have a height compensation device for compensating for sagging of the examination tabletop when loaded by a patient of predetermined stature in a predetermined way. The examination tabletop is in the treatment or diagnosis area, and the height compensation device can be set to different load states or conditions of the examination tabletop.

Another object is also attained by a method for setting an examination tabletop, which is adjustable in vertical and in longitudinal directions, of a patient examination support system, and in which the examination tabletop may protrude in the longitudinal direction past a lifting structure, and a treatment or diagnosis area is disposed in the area of the examination table protruding past the lifting structure, and wherein to compensate for a sagging of the examination table in the treatment or diagnosis area, the lifting structure may be adjusted in such a way that for a predetermined patient stature and patient position, the positioning of the weight-loaded examination tabletop in the treatment or diagnosis area corresponds substantially to a positioning of the unloaded examination tabletop.

The sagging of the examination tabletop caused by the weight of the patient of predetermined stature of an examination tabletop loaded in a predetermined way, that is, loaded by the position of the patient, may be compensated for by means of a height compensation device of a lifting structure that supports the examination tabletop.

Another concept is that a patient on an examination tabletop for a diagnosis system, in particular a computed tomography system, or treatment system, in particular for radiation therapy, typically lies in a defined position or in one of a plurality of defined positions. For a patient of a certain height and a certain weight, there is accordingly a fixed relationship between sagging of the examination tabletop in a fixedly specified treatment and/or diagnosis area and a displacement or adjustment of the examination tabletop relative to the lifting structure, also known as a longitudinal stroke of the examination tabletop. Once this relationship has initially been taken into account in the adjusting device for the examination tabletop, it is then assured that the examination table loaded by the patient will be substantially correctly positioned in the treatment or diagnosis area. The height compensation device is preferably set fixedly to a patient of medium stature, that is, of medium height and medium weight.

In a preferred embodiment, the height compensation device can be set to different load states or conditions of the examination tabletop. The term load state may be understood here to mean both the position of the patient on the examination tabletop and the weight and height of the patient. Preferably, only a rough classification is made here, for instance into categories or types of light weight, medium weight and heavy patients; by specifying the "patient type", for instance by pressing a button on the patient examination support system or a control unit, the height compensation device is set in whatever way is suitable at the time of the examination.

If the diagnosis system uses radiation, particularly x-rays, the examination tabletop may be radiation transparent at least partly but preferably completely. However, the invention is equally applicable for surgical systems which require a positioning of the patient in a substantially exactly defined position.

The weight load of the patient may cause the examination tabletop, spaced apart from the lifting structure in the treatment or diagnosis area, to be at least slightly skewed relative to a portion of the examination tabletop that is mounted on the lifting structure. To make an exact horizontal alignment of the examination tabletop in the treatment or diagnosis area possible, the examination tabletop is preferably rotatably perpendicular to the longitudinal direction of the examination tabletop about a transverse axis, that is, a horizontal axis. As such, the examination tabletop may be slightly inclined only in a region of the lifting structure, but in that region a skewed position of the examination tabletop may not be relevant.

One advantage is in particular that the patient load need not be measured, which may entail additional efforts and expenses. Because the patient weight load is taken into account once and for all, good to very good compensation for sagging of the examination table is attained over a broad weight range. For instance, based on a "100 kg standard patient" and a variation in the patient load from 50 to 150 kg, sagging may be reduced by approximately 50 to 100%.

Further advantages and features recited in connection with the examination support system may apply analogously to a corresponding method as well.

Illustrative and exemplary embodiments of the invention are described in further detail below with reference to and in conjunction with the figures.

BRIEF DESCRIPTION OF THE DRAWINGS

Parts and parameters corresponding to one another are provided with the same reference numerals in all the drawings.

FIG. 1 schematically shows a patient examination support system 1 with a lifting structure 2 and an examination tabletop 3 that is adjustable in height by the lifting structure 2; the examination tabletop 3 is longitudinally and displaceably supported on a trolley 4 that forms a fastening system. The vertical and longitudinal adjustability of the examination tabletop 3 are each indicated by a double-headed arrow. The examination tabletop 3 is horizontally displaceable up to a maximum longitudinal adjustment $L_{max}$ of, for example, 1500 mm and in the process passes through a receiving or diagnosis area 5, spaced apart longitudinally from the lifting structure 2, of a CT system, representing a diagnosis system 6. A sagging D caused by the weight of the examination table 3 and primarily by the weight of the patient is shown exaggerated in FIG. 1. In the area of the diagnosis system 6 remote from the lifting structure 2, that is, to the right of the CT system 6 in the drawing, the examination tabletop 3 is not additionally braced.

The sagging D of the examination tabletop 3 is intended to be compensated for, in particular in an imaging plane or scanning plane E inside the diagnosis area 5. FIG. 2 shows a basic relationship between a longitudinal stroke L of the examination tabletop 3 and the sagging D in the scanning plane E. The vertical and horizontal axes may have different scales.

Figure 1:
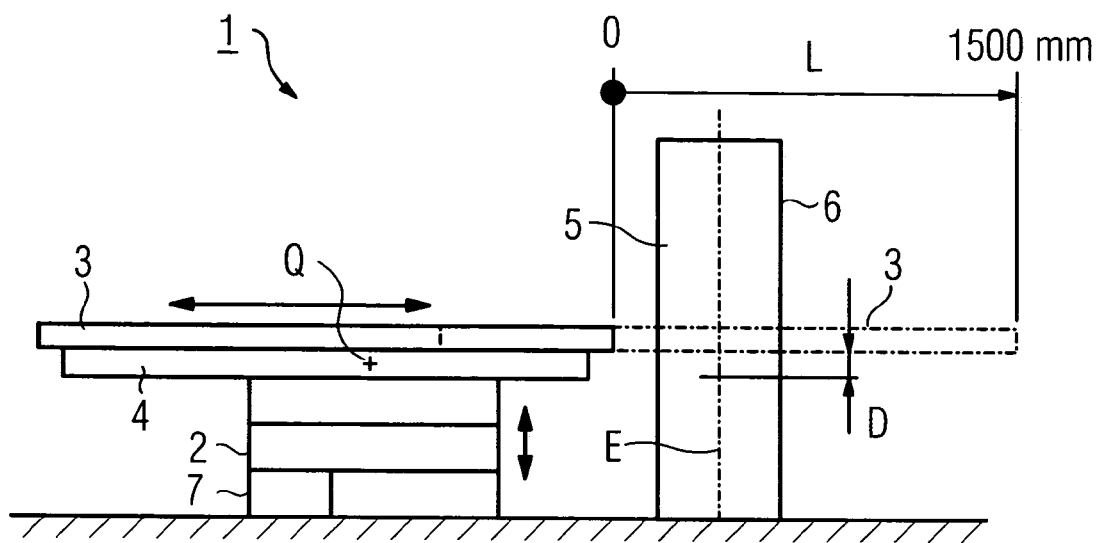
FIG. 1 is a schematic cross-sectional view of a patient examination support system and a diagnosis system.
Figure 2:
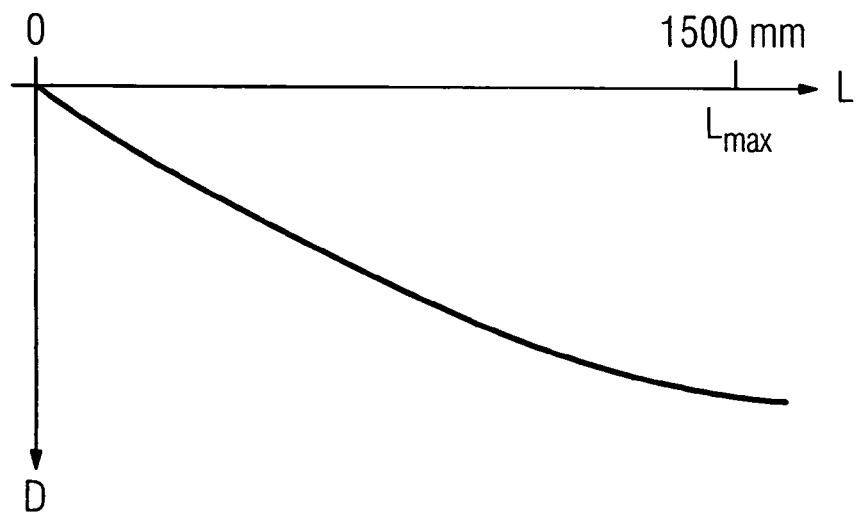
FIG. 2 is a graph illustrating a relationship between a longitudinal stroke and a sagging of the examination tabletop of the patient examination support system.
Figure 3:
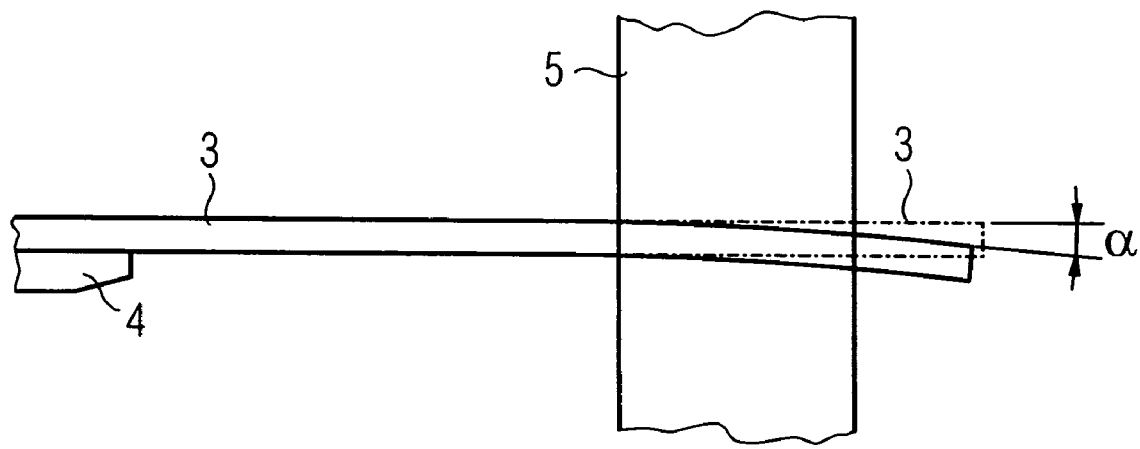
FIG. 3 is a fragmentary view of an examination tabletop with the sagging shown in an examination area.

The sagging of the examination tabletop 3 is shown in detail in FIG. 3. A bending angle α, which the examination tabletop 3 forms with a horizontal plane along the longitudinal stroke L in the vertical direction in the examination area 5, is also shown here in exaggerated form. To compensate for the sagging D in the scanning plane E, a height compensation device 7 (FIG. 1) is provided. By means of the height compensation device 7, which is realized using control technology and is preferably integrated with the adjusting device for the patient examination support system 1, the examination tabletop 3 may be adjusted higher by the lifting structure 2, by an amount substantially equal to the sagging D, as a function of the longitudinal stroke L. Thus, the height compensation device 7 of the patient examination support system 1 is used for a correction of the height setting. This correction compensates for the sagging of the examination tabletop 3. No measurement of the patient load is contemplated, which would entail additional effort and expense. Instead, the height compensation device 7 functions with a characteristic curve for a "standard patient", for instance, a patient weighing 80 kg and 1.8 m tall, lying on one end of the examination tabletop. As an alternative, in a preferred embodiment, it is provided that the height compensation device 7 can take or use data of different "patient types" stored in memory into account and sets the examination tabletop 3 suitably in each case with the aid of these data. Moreover, depending on the type of diagnosis system 6, the position of the patient ("head first", "feet first") can also be taken into account automatically in the setting of the height compensation device 7.

Thus, the compensation for the sagging D by the lifting table 2 is of primary significance; compensation for the bending angle a is of subordinate relevance. To make the patient positioning still more precise, compensation for the bending angle α, that is, a horizontal position the examination table 3 in the diagnosis area 5, may be accomplished in an exemplary embodiment by pivoting the examination tabletop 3 about a transverse axis Q that extends perpendicular to the diagnosis system 6, or a plane of the drawing in FIG. 1. In the height adjustment accomplished by means of the height compensation device 7, this slightly skewed position of the examination tabletop 3 in the region of the lifting structure 2 may be taken into account.

The invention claimed is:

1. A patient examination support system, comprising:
    an examination tabletop adjustable in vertical and in longitudinal directions; and
    a lifting structure which supports the examination tabletop,
    wherein a treatment or diagnosis area is spaced apart in the longitudinal direction of the examination tabletop from the lifting structure, and
    wherein the lifting structure has a height compensation device for compensating for a sagging of the examination tabletop apart from the lifting structure when loaded by a patient in the treatment or diagnosis area.

2. The patient examination support system of claim 1, wherein the height compensation device is adjustable to a plurality of load conditions of the examination tabletop.

3. The patient examination table system of claim 1, wherein the examination tabletop is rotatable about a transverse axis disposed perpendicular to the longitudinal direction of the examination table.

4. The patient examination table system of claim 1, wherein the height compensation device comprises a control unit with a memory device to store a plurality of patient load conditions for an instantaneous adjustment of the lifting structure.

5. The patient examination table system of claim 1, wherein the height compensation device for compensating for a sagging of the examination tabletop when loaded by a patient of predetermined stature in a predetermined way in the treatment or diagnosis area.

6. A method for setting an examination tabletop of a patient examination support system, the examination tabletop is adjustable in vertical and in longitudinal directions and protrudes in the longitudinal direction past a supporting lifting structure, the method comprises:
    loading a patient on the examination tabletop;
    positioning the protruding portion of patient loaded examination tabletop in a treatment or diagnosis area; and
    compensating for a sagging of the protruding portion of the examination tabletop apart from the lifting structure in the treatment or diagnosis area by adjusting the lifting structure for the patient stature and position on the examination tabletop, such that the positioning of the patient loaded examination tabletop in the treatment or diagnosis area corresponds substantially to a positioning of the examination table unloaded.

7. The method of claim 6, wherein the act of compensating for the sagging of the examination tabletop further comprises using a height compensation device for adjusting the lifting structure.

8. The method of claim 6, wherein the compensating act comprises compensating for the patient stature and position of the examination table.

9. A method for setting an examination tabletop of a patient examination support system, the examination tabletop is adjustable in vertical and in longitudinal directions and protrudes in the longitudinal direction past a supporting lifting structure, the method comprises:
   loading a patient on the examination tabletop;
   positioning the protruding portion of patient loaded examination tabletop in a treatment or diagnosis area of a diagnosis system; and
   compensating for a bending of the protruding portion of the examination tabletop apart from the lifting structure in the treatment or diagnosis area by pivoting the examination tabletop about a transverse axis that extends perpendicularly to the diagnosis system.

10. A patient examination support system, comprising:
   an examination tabletop adjustable in vertical and in longitudinal directions; and
   a lifting structure which supports the examination tabletop,
   wherein a treatment or diagnosis area is spaced apart in the longitudinal direction of the examination tabletop from the lifting structure,
   wherein the lifting structure has a height compensation device for compensating for a sagging of the examination tabletop when loaded by a patient in the treatment or diagnosis area, and
   wherein the examination tabletop is rotatable about a transverse axis disposed perpendicular to the longitudinal direction of the examination table.

11. The patient examination support system of claim 10, wherein the height compensation device is adjustable to a plurality of load conditions of the examination tabletop.

12. The patient examination table system of claim 10, wherein the height compensation device comprises a control unit with a memory device to store a plurality of patient load conditions for an instantaneous adjustment of the lifting structure.

13. The patient examination table system of claim 10, wherein the height compensation device for compensating for a sagging of the examination tabletop when loaded by a patient of predetermined stature in a predetermined way in the treatment or diagnosis area.

14. A patient examination support system, comprising:
   an examination tabletop adjustable in vertical and in longitudinal directions; and
   a lifting structure which supports the examination tabletop,
   wherein a treatment or diagnosis area is spaced apart in the longitudinal direction of the examination tabletop from the lifting structure,
   wherein the lifting structure, located on one side of the treatment or diagnosis area, has a height compensation device for compensating for a sagging of the examination tabletop on an other side of the treatment or diagnosis area when loaded by a patient in the treatment or diagnosis area.

* * * * *